United States Patent [19]

Erlich

[11] Patent Number: 4,772,275

[45] Date of Patent: Sep. 20, 1988

[54] SHEATH FOR DEVICES FOR INJECTING OR WITHDRAWING BODY FLUIDS

[75] Inventor: Frederick L. Erlich, Southfield, Mich.

[73] Assignee: PRN Services, Inc., Royal Oak, Mich.

[21] Appl. No.: 23,813

[22] Filed: Mar. 9, 1987

[51] Int. Cl.⁴ ............................................. A61M 25/00
[52] U.S. Cl. .................... 604/280; 604/263; 206/364; 206/438
[58] Field of Search ............... 604/171, 172, 280, 358, 604/385.1, 263, 162, 192, 197, 198; 206/306, 361, 363, 364, 365, 438; 128/763–765

[56] References Cited

U.S. PATENT DOCUMENTS

| | | | |
|---|---|---|---|
| 3,024,788 | 3/1962 | Lane | 604/385.1 |
| 3,185,150 | 5/1965 | Sorenson | 206/365 |
| 3,886,930 | 6/1975 | Ryan | 128/764 |
| 3,902,500 | 9/1975 | Dryden | 604/171 |
| 4,209,013 | 6/1980 | Alexander et al. | 123/213 A |
| 4,353,367 | 10/1982 | Hunter et al. | 128/213 A |
| 4,664,653 | 5/1987 | Sagstetter et al. | 604/192 X |

FOREIGN PATENT DOCUMENTS 1558162  2/1969  France ................ 604/280

*Primary Examiner*—Dalton L. Truluck
*Assistant Examiner*—Frank Wilkens
*Attorney, Agent, or Firm*—Arnold S. Weintraub

[57] ABSTRACT

A device for sterile disposal of a device used to withdraw or inject fluids from or into the body comprising a tubular sheath disposed in a rolled-up fashion around the body fluid device proximate one end thereof. The length of the sheath is great enough to permit the sheath, when unrolled, to extend beyond the end of the body fluid device and for a sufficient distance to permit ready enclosure thereof and subsequent sealing off of the contents of the sheath. A method for using the device is also disclosed. The device is particularly useful in combination with a catheter of conventional design.

19 Claims, 1 Drawing Sheet

SHEATH FOR DEVICES FOR INJECTING OR WITHDRAWING BODY FLUIDS

BACKGROUND OF THE INVENTION

1. Field of the Invention

This invention relates to the field of sterile disposal of device such as catheters, and the like used for injecting or withdrawing fluids into or from the body and, in particular, to a sheath disposed around such a device which may be drawn up to enclose the used device and tied off for sterile disposal thereof.

2. Description of the Prior Art

Catheters and other devices for use in draining off accumulated fluids from body cavities or injecting fluids into the body have been widely used in many medical fields for a long period of time. With reference to catheters, there are numerous types and designs, any of which are particularly adapted to be inserted into a particular body cavity. For example, an urethral catheter is designed to drain urine from the bladder. A ventricular catheter is adapted to drain excess cerebrospinal fluid from the brain. A peritoneal catheter is used to drain fluid from the peritoneum, as in kidney dialysis. An enema catheter is used to introduce fluid into the gastrointestinal track.

All of the above-mentioned types of catheters, as well as others too numerous to enumerate, have certain design features in common. A typical medicinal catheter is formed of hollow, flexible tubing. The tubing is typically comprised of a silicone elastomer such as silicone rubber, a substance which is soft and non-irritating to body tissues. A typical catheter will have a closed end and an open end. One or more inlets will be formed adjacent the closed end. An outlet will be formed adjacent the open end, and frequently will be comprised of the open end itself. Catheters designed for different purposes may additionally comprise other structures, but the ones enumerated are generally common to all catheters. Also, the dimensions of the catheter may vary greatly and will be adapted to the purpose for which it is intended. For example, a catheter adapted as an urinary catheter may typically have an outside diameter in the range of 0.3–0.8 millimeters. In contrast, a ventricular catheter will have a much smaller diameter.

No matter the particular type, most catheters are used in a similar manner. The closed end of the catheter carrying the outlets is inserted into the body cavity containing the fluid which needs to be drained inserted. The insertions process may be directly through a body orifice, such as is the usual case with urethral catheters, or a special opening may have to be made. For example, an opening may have to be made into a vein and the catheter threaded through the vein until it reaches the appropriate body cavity, such as is the case with ventricular catheters. After the catheter is inserted, some means of collecting the fluid must be attached to the open, outlet end. Sometimes, as for ventricular catheters, the outlet end of the catheter will remain within the body and the excess fluid drained will be absorbed by another area of the body. More commonly, however, the excess fluid will simply be collected in a bag or bottle and discarded. The catheter may be left in place for long periods of time, or the excess body fluid may be drained quickly and the catheter removed after only a short period of insertion.

Irrespective of what type of catheter is used, how long it remains in place, or what type of body fluid it is used to drain, all catheters must eventually be disposed of. When the catheter is no longer needed, it will be removed from the body and then must be disposed. If the catheter has been used with a patient suffering from a communicable or infectious disease, the catheter so used will be highly likely to be contaminated with an infectious agent. If such contaminated catheters are simply discarded in a casual manner, the possibility of contaminating attendant personnel and perhaps other patients is high.

The same disposal problem arises with other medical devices that come in contact with body fluids. For example, syringes are commonly used to inject or withdraw fluids from, for example, the circulatory system, the lymphatic system, the cerebrospinal system, etc. Most commonly, the syringes are disposable and used only once. Since they must be disposed of after each use, the possibility of contamination from a used syringe is quiet significant.

The problem of disposal of contaminated catheters and other devices is particularly acute in the management of patients afflicted with such highly infectious diseases as acquired immune deficiency syndrome (AIDS). For diseases such as AIDS, where the exact mechanism of transmission is poorly understood, it is extremely important that attending personnel be isolated as much as possible from all potential sources of infection. Even more significantly, the apprehension by persons attending AIDS patients that they may be contaminated with the disease by the mere handling of objects used in the treatment of the patients, such as used catheters or syringes, may interfere with the ability of the attending personnel to provide proper care and treatment of the patient.

Heretofore, the only solution to the problem of sanitary disposal of catheters and other devices used in the treatment of highly infectious patients have been ad hoc, unsatisfactory ones. For example, a used catheter may be removed from the patient and immediately placed within a sterile container, such as a plastic bag, the container then being sealed. However, due to the shape of the catheter and the flexible, resilient material from which it is typically made, it is difficult to place the unwieldy catheter within the container without having to attempt to fold it or roll it up. Obviously, the motions involved in doing this caused such unnecessary and dangerous handling of the contaminated catheter.

It would be desirable to provide a means for sterile containment and subsequent disposal of a device such as a catheter which has been in contact with body fluids which minimizes handling of the contaminated object.

It would also be desirable to provide a means of disposal which is mounted directly around the device and eliminates the necessity of a separate container.

It would also be desirable to provide a device and mounted means of disposal which could easily enclose and contain the used device by a simple, one-step unrolling motion.

It would also be highly desirable to provide a device mounted disposal means which is easy to use and has the additional advantages of being cheap to manufacture and sterilize.

SUMMARY OF THE INVENTION

The device and method disclosed and claimed herein provides for easy and effective containment of a medical device such as a catheter, syringe, cannula, drainage tube etc., which has been in contact with body fluids which is simple and inexpensive to manufacture, and may be easily disposed of. The invention provides a device for sterile disposal of devices used for injecting fluid into the body or withdrawing fluid from a body cavity, the device comprising a sheath formed of a thin, flexible, fluid impervious material which is disposed around the device in a rolled-up fashion. The sheath may be either permanently attached to the device by adhesive or sonic welding or may be snap fit thereon. The length of the sheath is such that, when it is unrolled, it will enclose the contaminated portion of the device and may be sealed off for sterile containment of the contents. With reference to an embodiment particularly suited for disposal of a catheter, the device comprises in combination: a hollow, tubular catheter having at least one inlet disposed proximate a closed end and at least one outlet disposed proximate an open end; and a tubular catheter sheath disposed around the catheter medial of the closed end thereof. The length of the catheter sheath is great enough to permit it to extend beyond the closed end of the catheter for a sufficient distance such that the closed end may be enclosed by the sheath, with a sufficient additional length to permit ready sealing off of the contents of the sheath. The catheter sheath is disposed around the catheter in a rolled-up fashion.

To use the sheath of the instant invention, the contaminated device is first removed form the patient. the rolled-up sheath is simply unrolled to its full length After it is unrolled, it will extend beyond the contaminated end of the used device. The end of the sheath may be then sealed to completely contain the inlet and the contaminated portion of the device therein. The device encased in the sheath may be then simply discarded. Alternatively, the sheath may be unrolled as the device is being withdrawn.

In some cases it will be desirable to also enclose the other end of the device. This is particularly true of catheters. While is most cases, the outside of the outlet end of the catheter will not normally be contaminated, this will not be the case for catheters which are completely internally disposed within the patient. Additionally, it is also possible that the outside of the outlet end of any type of catheter may become contaminated through malfunction, improper use, splashing, etc. therefore, to provide sterile disposal of virtually the entire length of the catheter, one embodiment of the instant invention provides a second, outlet sheath disposed adjacent the catheter sheath and medial of the outlet end of the catheter. Like the catheter sheath, the outlet sheath has a length sufficiently long to enclose completely the outlet end of the catheter and permit subsequent sealing off of the contents of the outlet sheath. In order to use this embodiment, the outlet sheath is unrolled to enclose the outlet end and sealed as described above. Subsequently, the catheter sheath is unrolled to contain and enclose the inlet end of the catheter. Its end is then sealed off in the same manner. In a similar manner, the dual sheaths could be used to completely enclose any device contaminated along most of its length with body fluids.

In order to isolate the infectious material contained within the sheaths, it is highly desirable that they be formed of a material which is both flexible and impervious. The material should be impervious to body fluid, vapors formed thereof, atmospheric air, gases, and microorganisms. The material must also be flexible enough to permit ready rolling up of the sheath during manufacture. Additionally, the material must be one that can be either fabricated in a sterile manner or one which can withstand sterilization after manufacture. Typical examples of such a material include: polyethylene; high density polyethylene; polypropylene; polytetrafluoroethlyne; polyvinyldene fluroide; polyvinylchorlride; polyethylene teraphathalate; silicone elastomers; other synthetic organic polymers; and the like. For a device such as a syringe, where there may be a possibility of puncture of the sheath by the device, the material should also be resistant to tearing and puncture.

BRIEF DESCRIPTION OF THE DRAWING

The various features, advantages and other uses of this invention will become more apparent by referring to the following detailed description and drawing in which.

DESCRIPTION OF THE PREFERRED EMBODIMENTS

Figure 1:
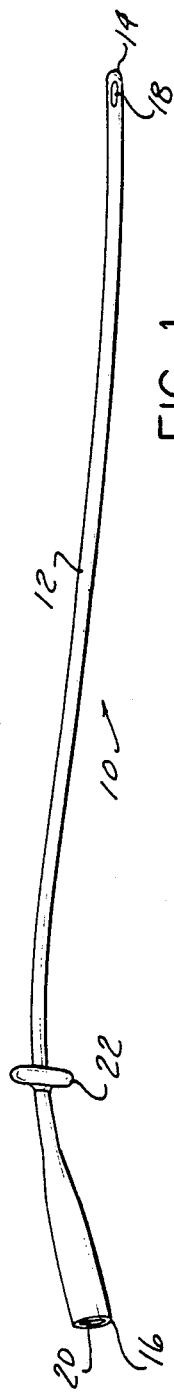
FIG. 1 is a perspective view of a device fabricated in accordance with the teachings of the instant invention showing a catheter sheath in a rolled-up position disposed around a typical catheter.

Throughout the following description and drawing, identical reference numerals are used to refer to the same components shown in multiple figures of the drawing.

Referring now to the drawing, and to FIG. 1 in particular, there is shown a device 10 for sterile disposal of a catheter 12 for use in a body cavity. While the embodiment showing in the drawing are particularly adapted to catheters, it is to be understood that this is for illustrative purposes and that the instant invention is applicable to any device that comes in contact with body fluids. The catheter 12 is hollow and tubular, and has a closed end 14 and an open end 16. At least one outlet 18 is formed in the wall of the tubular catheter 12 adjacent the closed end 14 thereof. An outlet 20 is formed adjacent the open end 16 of the catheter 12, and, as shown in FIG. 1, the outlet 20 may be formed by the open end 16.

Disposed around and attached to the catheter 12 is a catheter sheath 22. The catheter sheath is disposed around the catheter 12 medial the closed and open ends thereof. A typically placement of catheter sheath 22 is depicted in FIG. 1, where catheter sheath 22 is shown disposed around catheter 12 in near proximity to outlet 20. By disposing catheter sheath 22 in near proximity to the outlet 20 of catheter 12, the catheter sheath 22, when unrolled, will enclose and contain most of the length of catheter 12. The catheter sheath 22 is attached to the catheter 12 by a suitable means such as sonic welding, a suitable adhesive or bonding agent, etc. Alternately, the catheter sheath 22 may be attached to the catheter 12 by a snap fit.

As depicted in FIG. 1, catheter sheath 22 is shown rolled up around catheter 12. FIG. 12 depicts catheter 22 after it has been unrolled for its entire length. It will be seen from an examination of FIG. 2 that the length of catheter sheath 22 is long enough such that it will extend beyond the closed end 14 of catheter 12. The extension of catheter sheath 22 beyond closed end 14 will permit the sealing off thereof to enclose the contents of catheter sheat 14. Means of sealing 24 is provided to seal off the end of catheter sheath 22 to completely enclose the contents thereof. Means of sealing 24 may be in a conventional type of sealing means, such as a paper coated wire twist tie, a rubber band, adhesive tape, a slip, a spring clip, etc. Alternatively, the end of sheath 22 may be provided with a self-sealing means such as a lip and groove formed therein.

The method of use of the device 10 for sterile disposal of a used device, e.g., a catheter will now be described. First, it is desirable that device 10 be made sterile prior to use. The device 10 may be either manufactured in a manner such that it is sterile or that it may be sterilized after manufacture by any conventional method. Prior to use, the catheter sheath 22 will be in the rolled up position shown in FIG. 1.

The catheter is used in the conventional manner by inserting the closed end 14 with the inlet 18 formed therein into a body cavity (not shown). The outlet 20 of the catheter 12 will be attached to a means (not shown) for storing the unwanted fluids. In certain cases, outlet 20 may be first connected with an auxiliary tube (not shown) which is in turn connected to the storage means.

Figure 2:
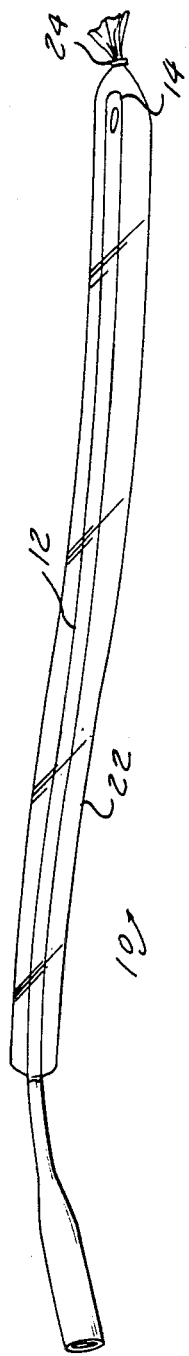
FIG. 2 illustrates the device of FIG. 1 with the catheter sheath having been unrolled and sealed off.

After the body fluid has been drained, the catheter will be removed from the body cavity by removing closed end 14 carrying inlet 18 therefrom. The outlet 20 disposed on open end 16 will be then detached from the storage means and/or auxiliary tube. The catheter sheath 22 will be then be unrolled by grasping it and pulling it toward closed end 14. After it is fully unrolled and extends beyond the closed end 14 of the catheter 12, it will be sealed off by applying sealing means 24. FIG. 2 illustrates the appearance of the device of the instant invention after the steps of unrolling and sealing off have been performed. It may be seen from an examination of FIG. 2 that the contaminated portions of the catheter 12, including particularly inlet 18, are fully contained within the sealed off catheter sheath 22. Since the catheter sheath 22 remained in a rolled-up position while the catheter was in use, the surface exposed during the unrolling procedure will not have been exposed to the contaminated body fluids. Thus, the impervious area provided by the unrolled and sealed off catheter sheath 22 will effectively prevent cross-contamination between the used catheter and any other object, such as other hospital equipment or another patient or attendant.

Alternately, the catheter sheath 22 may be unrolled as the catheter 12 is being withdrawn from the body. It is then sealed off as described above. This alternate method provides even stronger protection against the possibility of contamination.

Figure 3:
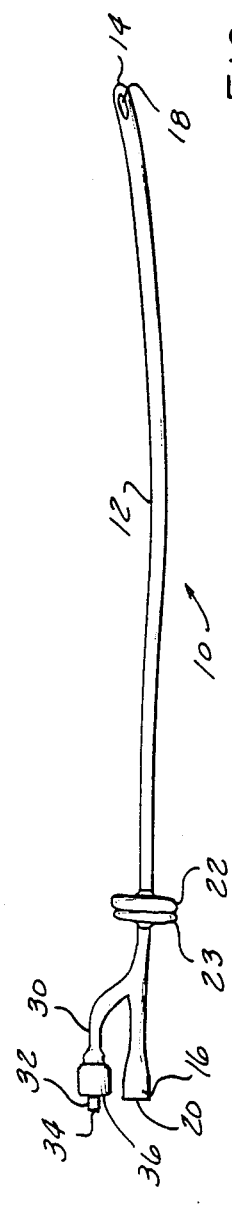
FIG. 3 is a perspective view of an alternative embodiments of the device of the present invention in which a secondary sheath is provided.
Figure 4:
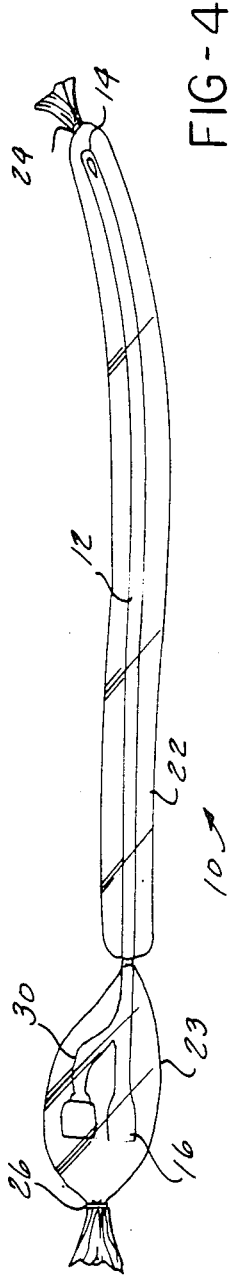
FIG. 4 illustrates the device of FIG. 3 with both sheaths unrolled and sealed off.

Another embodiment of the device of the instant invention is illustrated in FIGS. 3 and 4. The catheter 12 shown in FIG. 3 has the additional structure of a branch 30 formed near the open end 16 of the catheter 12. The branch 30 is hollow and tubular and is in fluid communication with catheter 12. A hollow, rigid member 32 is shown partially inserted into the end of branch 30. Disposed within hollow, rigid insert 32 is a plug 34 comprised of softer material, typically silicone rubber. A rubber band 36 is shown disposed on the outside of branch 30 to hold rigid insert 32 and plug 34 in correct position. The purpose of the additional structures shown is so that the needle of a syringe (not shown) may be inserted into catheter 12. The needle of the syringe into catheter 12 by plunging it into plug 34. By means of the syringe, several additional functions may be added to the functioning of the catheter. For example, if additional suction is needed to withdraw the body fluids from the cavity, the suction may be supplied by means of a syringe. Conversely, medication may be inserted into the body cavity by means of the syringe.

In FIGS. 3 and 4, an outlet sheath 23 is provided. FIG. 3 illustrates the outlet sheath 23 in its rolled-up position. Outlet sheath 23 is disposed immediately adjacent catheter sheath 22 and medially of the open end 16 of catheter 12. As with catheter sheath 22, the length of outlet sheath 23 is such that, when catheter sheath 23 is fully unrolled, a portion thereof will extend beyond the open end 16 of catheter 12. Outlet sheath 23, upon being unrolled, may then be sealed off with sealing means 26 in a manner analogous to catheter means 22.

FIG. 4 depicts the device of FIG. 3 with both sheaths 22, 23 unrolled and sealed off. It may be seen from an examination of FIG. 4 that virtually the entire length of catheter 12 is encased by sheaths 22, 23, thereby preventing contamination from virtually any part of catheter 12 from reaching the environment outside the sheaths 22, 23. Sterile containment of the entire catheter 12 may be necessary in cases where both ends 14, 16 thereof are likely to become contaminated.

In summary. there has been disclosed a sheath for sterile containment and disposal of a device used to inject or withdraw fluid into or from the body. The device comprises a tubular sheath disposed in rolled-up fashion around the device and in close proximity to an end thereof. The length of the sheath, when unrolled, is great enough to permit the unrolled sheath to extend beyond the end of the device for a sufficient distance such that the end of the sheath may be sealed, thereby providing complete and sanitary containment of the contents thereof.

While the device and method of the present invention has been described with regard to certain embodiments and exemplifications thereof, they are not intended to be so limited but solely by the claims appended hereto.

I claim:
1. A sterile disposal device, which comprises:
a flexible catheter apparatus which is used in contact with body fluids, the apparatus having a body contact end and a non-body contact end; and
a sheath disposed around the flexible catheter apparatus medial of the ends thereof, the sheath having a rolled-up position and an unrolled position, the sheath being in the rolled-up position when the flexible catheter apparatus is in contact with the body fluids, the length of the sheath being sufficient to permit the sheath to extend beyond the body contact end of the flexible catheter apparatus for a sufficient distance and permit ready closure and sealing thereof.

2. The device of claim 1, wherein the sheath is in the unrolled position and secured around the body contact end when the flexible catheter apparatus is removed from the body.

3. The device of claim 1 wherein the sheath is formed of a flexible, impervious material.

4. The device of claim 3 wherein the flexible material is impervious to body fluids, vapors thereof, air, gases, and micro-organisms.

5. The device of claim 1 wherein all of the components are in a sterile condition prior to use.

6. The device of claim 1 further comprising means of sealing the sheath.

7. A sterile disposal device, which comprises:
flexible catheter apparatus which is used in contact with body fluids, the flexible catheter apparatus having a body contact end and a non-body contact end;
a first sheath disposed around the flexible catheter apparatus medial of the ends thereof, the first sheath having a rolled-up position and an unrolled position, the first sheath being in the rolled-up position when the flexible catheter apparatus is in contact with the body fluids, the length of the first sheath being sufficient to permit the first sheath to extend beyond the body contact end of the flexible catheter apparatus for a sufficient distance and permit ready closure and sealing thereof; and
a second sheath disposed disposed around the flexible catheter apparatus adjacent to the first sheath and medial of the non-body contact end of the flexible catheter apparatus, the second sheath having a rolled-up position and an unrolled position, the length of the second sheath being great enough to permit the second sheath to extend beyond the non-body contact end of the flexible catheter apparatus for a sufficient distance and permit ready closure and sealing thereof.

8. The device of claim 7, wherein the second sheath is in the rolled-up position when the body contact end is in contact with the body fluids.

9. The device of claim 7 wherein the sheath and the outlet sheath are formed of a flexible, impervious material.

10. The device of claim 9 wherein the flexible material is impervious to body fluids, vapors thereof, air, gases and micro-organisms.

11. The device of claim 7 wherein all of the components are in a sterile condition prior to use.

12. A device for the sterile disposal of a catheter for use in a body comprising in combination:
a hollow, tubular catheter having at least one inlet disposed proximate a closed inlet end and at least one outlet disposed proximate an open end; and
a tubular catheter sheath formed of a flexible, impervious material disposed around the catheter in a rolled-up fashion medial of the inlet and outlet ends thereof, the sheath having a rolled-up position and an unrolled position, the sheath being in the rolled-up position when the apparatus is in contact with the body fluids, the length of said catheter sheath being great enough to permit the catheter to extend beyond the inlet end of the catheter sheath for a sufficient distance and permit ready enclosure thereof and subsequent sealing off of the contents of the sheath.

13. The device of claim 12 further comprising a tubular outlet sheath formed of a flexible, impervious material disposed in a rolled-up fashion adjacent the catheter sheath and medial of the outlet end and the catheter sheath, the length of said outlet sheath being great enough to permit the outlet sheath to extend beyond the outlet end of the catheter for a sufficient distance and permit ready enclosure thereof and subsequent sealing off of the outlet sheath.

14. The device of claim 12 further comprising means of sealing the catheter sheath.

15. The method of sterile disposal of a catheter used in a body cavity comprising the steps of:
providing a hollow, tubular catheter having at least one inlet disposed proximate a closed end and at least one outlet disposed proximate an open end;
providing a rolled-up catheter sheath disposed around the catheter medial of the closed and open ends thereof, the length of said catheter sheath being great enought to permit the catheter sheath to extend beyond the closed end of the catheter for a sufficient distance and permit ready enclosure thereof and subsequent sealing off of the contents of the catheter sheath;
using the catheter in the body cavity;
removing the catheter from the body cavity and unrolling the catheter sheath for extension thereof;
enclosing the closed end of the catheter in the catheter sheath; and
sealing off the end of the catheter sheath.

16. The method of claim 15 comprising the further step of sterilizing the catheter and catheter sheath prior to use.

17. The method of claim 15 further comprising the step of:
providing a tubular outlet sheath disposed adjacent the catheter sheath, the length of said outlet sheath being great enough to permit the outlet sheath to extend beyond the closed end of the catheter for sufficient distance and permit ready and enclosure thereof and subsequent sealing off of the outlet sheath;
unrolling the outlet sheath for extension thereof;
enclosing the closed end of the catheter in the outlet sheath; and
sealing off the end of the outlet sheath.

18. The method of claim 17 wherein the catheter sheath is formed of a flexible, impervious material.

19. The method of claim 17 wherein the outlet sheath is formed of a flexible, impervious material.

* * * * *